United States Patent [19]

Erpenbach et al.

[11] 4,442,304

[45] Apr. 10, 1984

[54] PROCESS FOR PURIFYING AND RECOVERING CONTAMINATED CATALYST SOLUTION OBTAINED IN THE CARBONYLATION OF METHYL ACETATE AND/OR DIMETHYLETHER

[75] Inventors: Heinz Erpenbach, Cologne; Klaus Gehrmann; Winfried Lork, both of Erftstadt; Peter Prinz, Hürth, all of Fed. Rep. of Germany

[73] Assignee: Hoechst Aktiengesellschaft, Fed. Rep. of Germany

[21] Appl. No.: 402,942

[22] Filed: Jul. 29, 1982

[30] Foreign Application Priority Data

Aug. 31, 1981 [DE] Fed. Rep. of Germany ....... 3134350

[51] Int. Cl.$^3$ ...................... C07C 67/36; C07C 69/16; C07C 51/56; B01J 31/40
[52] U.S. Cl. ................... 560/232; 260/546; 260/549; 502/24; 502/33; 562/517
[58] Field of Search ............... 252/414, 420, 413, 412; 260/549, 546; 562/607, 517; 423/22; 560/232

[56] References Cited

U.S. PATENT DOCUMENTS

| | | | |
|---|---|---|---|
| 3,821,311 | 6/1974 | Hughes et al. ...................... | 568/452 |
| 4,013,584 | 3/1977 | Knifton .............................. | 252/415 |
| 4,287,089 | 9/1981 | Cohvers et al. ..................... | 252/414 |
| 4,333,884 | 6/1982 | Kubbeler et al. ................... | 260/546 |

*Primary Examiner*—P. E. Konopka
*Attorney, Agent, or Firm*—Connolly and Hutz

[57] ABSTRACT

The disclosure relates to a process for purifying and recovering a contaminated catalyst solution which is obtained in the carbonylation of methyl acetate and/or dimethylether, the catalyst solution containing carbonyl complexes of noble metals of group VIII of the Periodic System of the elements, quaternary heterocyclic aromatic nitrogen compounds or quaternary organophosphorus compounds as organic promoters, undistillable organic contaminants as well as acetic acid, acetic anhydride and ethylidene diacetate. To this end, the disclosure provides for the catalyst solution to be distillatively freed from its volatile constituents and for the remaining solid distillation residue to be water-treated, the noble metal/carbonyl-complex being precipitated together with the organic contaminants and the organic promoter becoming dissolved; for the precipitated and contaminated noble metal/carbonyl-complex to be removed by filtration and to be freed from the organic contaminants by extraction with aliphatic ethers; for the organic promoter to be recovered by evaporating the water or extracting it with halogenated hydrocarbons and for these latter to be evaporated; and for the purified noble metal/carbonyl-complex and the recovered organic promoter to be recycled into the carbonylation reaction.

14 Claims, No Drawings

PROCESS FOR PURIFYING AND RECOVERING CONTAMINATED CATALYST SOLUTION OBTAINED IN THE CARBONYLATION OF METHYL ACETATE AND/OR DIMETHYLETHER

The present invention relates to a process for purifying and recovering a contaminated catalyst solution which is obtained in the carbonylation of methyl acetate and/or dimethylether, the catalyst solution containing carbonyl complexes of noble metals of group VIII of the Periodic System of the elements, quaternary heterocyclic aromatic nitrogen compounds or quaternary organophosphorus compounds as organic promoters, undistillable organic contaminants as well as acetic acid, acetic anhydride and ethylidene diacetate.

The recovery of rhodium or rhodium carbonyl complexes from catalyst systems contaminated with residues or from distillation residues has already been described, basically in connection with hydroformylation processes. The process described in DE-PS No. 12 90 535, for example, provides for rhodium-containing hydroformylation residue to be treated with an aqueous organic acid, the rhodium complex becoming dissolved and separated from the organic phase, rhodium being recovered in a yield of 82 up to 94%.

The process described in DE-AS No. 12 95 537 provides for the rhodium-containing reaction residue to be treated with steam under a pressure of 2 to 31 bars at 100° to 250° C. The catalyst becomes decomposed and rhodium sludge, which as such cannot be used again in the carbonylation reaction, is recovered by filtration under pressure.

Further processes for recovering rhodium and or regenerating catalyst have been described in DE-OS No. 24 48 005 and DE-OS No. 26 14 799. As disclosed therein, the contaminated distillation residues originating from hydroformylation reactions are subjected initially to treatment with oxygen-containing mineral acids and peroxides, the treatment being intended to destroy rhodium and iridium carbonyl complexes and degrade the residues. After decomposition of peroxides in excess, the aqueous metal salt solutions are worked up by different methods. One of such method described in DE-OS No. 24 48 005 provides for the aqueous rhodium or iridium salt solution to be admixed at 0° up to 150° C. under a pressure of 1 up to 250 bars with a water-soluble organic solvent, a hydrohalic acid or an alkali metal halide and a tertiary phosphine, and for the metals to be precipitated from the solution in the form of rhodium or iridium-carbonyl complexes with the use of carbon monoxide and additionally under hydrating conditions. As disclosed in DE-OS No. 26 14 799, rhodium+++ is first absorbed from the aqueous solution on a cation exchanger and then desorbed by means of hydrochloric acid. The hydrochloric acid solution is admixed with tertiary phosphines, treated with CO and, if desired, hydrogen, and rhodium is precipitated as a carbonyl complex.

The processes described, for example, in DE-OS Nos. 24 50 965; 28 36 084; 29 39 839 or 29 41 232 are, however, not of assistance in the purification and recovery of noble metal/carbonyl-complexes (Rh, Ir, Pd, Ru) and their promoters from the contaminated catalyst solutions obtained in the carbonylation of methyl acetate or dimethylether. The catalyst solution obtained in the carbonylation reaction is composed of 0.1 up to 10 weight % noble metal/carbonyl complex, 40–70 weight % organic promoter, 1–10 weight % undistillable organic contaminants, and 20–40 weight % acetic acid, acetic anhydride and ethylidene diacetate. As can be inferred from the composition just indicated, it is possible for the catalyst solution to contain up to 80 weight % undistillable substances. After removal of volatile constituents by distillation, it is naturally possible to subject the noble metal/carbonyl-complex to oxidative degradation but this would entail the destruction of the entire quantity of organic promoters whereby the beneficial effect which is associated with catalyst work up would be jeopardized from the onset.

Subjecting the residue to treatment with aqueous organic acids also entails adverse effects as the noble metal carbonyl-complex undergoes dissolution as well as the bulk of undistillable organic contaminants, which then cannot be separated from catalyst and promoter.

On subjecting the catalyst to decomposition with steam at elevated temperature, noble metal in elementary form, whose reconversion to the active catalyst complex is very expensive is obtained. In addition to this, water-insoluble organic residue which cannot readily be separated from the elementary noble metal is obtained.

The present invention which enables the adverse effects described hereinabove to be avoided now provides a process wherein distillative and extractive operation permit contaminated catalyst solution which is obtained in the carbonylation of methyl acetate and/or dimethylether to be worked up in such a manner that it is possible for the noble metal/carbonyl-complex as well as for its promoters to be used again in the catalyst cycle, undistillable organic contaminants being removed therefrom. The present process compares favorably with the work-up methods described heretofore inasmuch as the extractants used for effecting work-up are cycled and substantially prevented from polluting the environment. Only those undistillable organic contaminants which are formed during the process and reaction are removed for disposal by incineration, for example, in accordance with the pertinent art.

The present processes comprises more particularly: distillatively freeing the catalyst solution from its volatile constituents and water-treating the remaining solid distillation residue, the noble metal/carbonyl-complex being precipitated together with the organic contaminants and the organic promoter becoming dissolved; removing the precipitated and contaminated noble metal/carbonyl-complex by filtration and freeing it from the organic contaminants by extraction with aliphatic ethers; recovering the organic promoter by evaporating the water or extracting it with halogenated hydrocarbons and evaporating these latter; and recycling the purified noble metal/carbonyl-complex and the recovered organic promoter into the carbonylation reaction.

Further preferred features of the present invention provide:
(a) for the distillation residue to be water treated at 40° to 80° C.;
(b) for 10 to 100 parts by weight water to be used per part by weight distillation residue;
(c) for the noble metal/carbonyl-complex filtered off to be extracted with diethyl- or diisopropylether;
(d) for the quaternary organophosphorus compounds to be recovered from their aqueous solution by extraction with methylene chloride or chloroform;
(e) for the catalyst solution to additionally contain carbonyl-yielding common metals as inorganic promoters which, during the water-treatment of the solid distillation residue, are (1) precipitated together with the organic contaminated noble metal/carbonyl-complex, filtered off, purified by extraction with an ether and recycled together with the noble metal/carbonyl-complex to the carbonylation reaction, and/or (2) dissolved together with the organic promoter and recovered by evaporation of the water or by extraction with halogenated hydrocarbons and evaporation of these latter, and recycled together with the organic promoter to the carbonylation reaction.

With respect to the origin of the contaminated catalyst solution, it is interesting to state that the reaction mixture coming from the carbonylation reactor is separated distillatively into desirable final products, especially acetic anhydride, acetic acid and/or ethylidene diacetate, and unreacted cycled feed material on the one hand, and into catalyst solution as base material on the other hand. A portion of this catalyst solution which becomes gradually contaminated is taken from the catalyst solution cycle and distillatively freed in accordance with this invention, preferably at 100°–120° C. and 1–100 millibars from volatile matter, e.g. acetic acid, acetic anhydride and ethylidene diacetate.

The noble metals customarily contained in the contaminated catalyst solutions comprise rhodium, iridium, palladium and/or ruthenium which are present as carbonyl complexes e.g. of the formula $[CH_3P(C_4H_9)_3]_2Rh(CO)I_5$ or $CH_3P(C_4H_9)_3Rh(CO)_2I_2$. As organic promoters, the catalyst solutions generally contain one or more of the following heterocyclic aromatic nitrogen compounds or organophosphorus compounds:

(1) N-methylpyridinium iodide; N,N-dimethylimidazolium iodide; N-methyl-3-picolinium iodide; N-methyl-2,4-lutidinium iodide; N-methyl-3,4-lutidinium iodide, N-methyl-quinolinium iodide;

(2) tri-n-butyl-methyl phosphonium iodide; trioctyl-methyl-phosphonium iodide; trilauryl-methyl-phosphonium iodide; triphenyl-methyl-phosphonium iodide.

The catalyst solution may finally contain, as inorganic promoters, compounds of carbonyl-yielding common metals selected from Ce, Ti, Zr, Hf, Ge, Sn, Pb, V, Nb, Ta, As, Sb, Bi, Cr, Mo, W, Mn, Re, Fe, Co, Ni.

Next, the distillation residue which remains behind should be introduced, preferably with agitation, into water and heated to 70° C., for example. The organic promoter portion contained in the distillation residue becomes dissolved in the water phase, whilst the noble metal/carbonyl complex and the undistillable organic contaminants formed during the reaction remain undissolved. Residue insoluble in the water phase is filtered off and subjected to extraction with an ether. The ether makes it possible for the organic contaminants to be extracted from the water-insoluble residue and a decontaminated noble metal/carbonyl-complex which can directly be recycled is obtained as extraction residue.

Undistillable organic contaminants which are dissolved in the ether phase are incinerated after the ether has been expelled. The promoter dissolved in the water phase is recovered in the form of pure material, after evaporation of the water, and used again in the reaction. In the event of the organic promoters being selected from quaternary organo-phosphorus compounds, it is possible for the promoter which is dissolved in the water phase to be also extracted with the use of halogenated hydrocarbons. This naturally means an economy of the expenses incurred by the evaporation of water. After evaporation of the extractant, pure organic promoter is obtained which is recycled to the catalyst solution cycle. The water raffinate is freed from the dissolved halogenated hydrocarbon by stripping. Next, water phase, halogenated hydrocarbons and ethers can be used again. Needless to say, the process of this invention can be carried out continuously or discontinuously.

EXAMPLE 1

250 g catalyst solution cycled for methyl acetate carbonylation was taken from the catalyst cycle consisting of rhodium carbonyl complex ($L_2Rh(CO)I_5$; L=ligand), tri-n-butylmethylphosphonium iodide as an organic promoter, acetic anhydride, acetic acid, ethylidene diacetate, and contaminants and freed from distillable materials under reduced pressure of about 2 millibars and at a base temperature of up to 120° C. 81.5 g (32.6 weight %) distillate (25.8 weight % acetic acid, 73.8 weight % acetic anhydride and 0.4 weight % ethylidene diacetate) and 168.5 g distillation residue containing 0.433 g rhodium and 145.71 g tri-n-butylmethylphosphonium iodide (=2 weight % Rh-carbonyl complex and 58.3 weight % TBMPI, based on 250 g catalyst solution) were obtained. The distillation residue was placed in a mortar, comminuted therein and then introduced with vigorous agitation into 5000 ml water at 20°–25° C. After 30 minutes, the suspension was heated to 60°–70° C. while agitation was continued. After altogether 1.5 hours, the residue was filtered, after-washed with water and dried for 1.5 hours at 120° C. under 2 millibars, 22.75 g material was obtained. Analysis indicated that it contained 0.432 g rhodium. The water-insoluble residue was introduced into a Soxhlet-apparatus and freed therein from undistillable organic contaminants by extraction with 500 ml diisopropylether at the boiling temperature of the ether. After extraction over a period of 3 to 5 hours and drying, the ether was found to contain 6.75 g insoluble residue containing 0.432 g rhodium. In other words, the ether-insoluble residue was found to contain practically all of the rhodium carbonyl complex used in the purification process. It was possible for it to be used again as such in the reaction. The diisopropylether phase was evaporated, and 16 g undistillable organic contaminants (=6.4 weight %, based on 250 g catalyst solution) which contained 0.01 weight % rhodium was retained in the flask; this corresponded to a 99.6% rhodium yield in the purification process. The ether which was distilled off was used again for purification.

The water phase originating from the filtration was also worked up under reduced pressure and 145.5 g tri-n-butylmethylphosphonium iodide, corresponding to a yield of 99.8%, was obtained as distillation residue. P/I-analysis with the use of 9 weight % P and 36.9 weight % iodine as well as IR-analysis and the melting point of 140° C. evidenced that the salt recovered was very pure. The presence of rhodium could here not be evidenced by analysis. The organic promoter salt as such was used again in the process, and the water phase evaporated was used again for extraction.

EXAMPLE 2

250 g catalyst solution cycled for dimethylether carbonylation was taken from the catalyst cycle consisting of acetic anhydride, acetic acid, ethylidene diacetate, rhodium arbonyl complex (LRh(CO)$_2$I$_2$; L=ligand), tri-n-butylmethylphosphonium iodide and undistillable organic contaminants, and freed from distillable matter under reduced pressure of 2 millibars at a base temperature of 120° C. 72 g (28.8 weight % distillate, 31 weight % acetic acid, 68.6 weight % acetic anhydride and 0.4 weight % ethylidene diacetate) and 178 g distillation residue containing 1.718 g rhodium and 156.3 g tri-n-butylmethylphosphonium iodide (=4.35 weight % Rh-carbonyl complex and 62.5 weight % TBMPI, based on 250 g catalyst solution) were obtained. The distillation residue was ground and introduced, with agitation into 6000 ml water at 20° C. After 30 minutes, the suspension was heated to 60°–70° C. while agitation was continued. After altogether 1.5 hours, the remaining residue was filtered, after-washed with water and dried at 120° C. under a pressure of 2 millibars. 21.75 g material was weighed. It was analyzed and found to contain 1.718 g rhodium. This residue was placed in a Soxhlet-apparatus and freed from undistillable organic contaminants by extraction with 500 ml diethylether at the boiling point of the ether. After extraction over a period of 3 to 5 hours and drying, 11.46 g ether-insoluble residue was obtained. It contained 1.71 g rhodium, corresponding to a yield of 99.5%. The ether-insoluble residue contained practically all of the rhodium carbonyl complex used in the purification. It was recycled to the reaction.

The diethylether phase was evaporated and 10.29 g undistillable organic contaminants (=4.12 weight %, based on 250 g catalyst solution) were retained in the flask. Analysis indicated that the residue still contained 0.09 weight % rhodium. The diethylether distilled off could be used again.

The water phase obtained by filtration was shaken 6 times, each time with 250 ml chloroform, for recovering the organic promoter. After evaporation of the chloroform, 156 g tri-n-butylmethylphosphonium iodide, corresponding to a yield of 99.8%, was obtained from the chloroform phase. P/I-analysis with 9 weight % P and 36.9 weight % iodine, IR-analysis and melting point indicated that the organic promoter salt recovered was very pure. The extracted water phase was freed from dissolved chloroform by stripping and could be used again. The chloroform was used in further operations for extracting organic promoter.

Instead of extracting the promoter dissolved in the water phase by shaking with chloroform, it is naturally possible for it to be extracted continuously with the use of a multiple stage column.

EXAMPLE 3

250 g catalyst solution cycled for methyl acetate carbonylation was taken from the catalyst cycle consisting of rhodium carbonyl complex (L$_2$Rh(CO)I$_5$; L=ligand), N,N-dimethylimidazolium iodide, undistillable organic contaminants, acetic acid, acetic anhydride and ethylidene diacetate, and freed from distillable matter under a reduced pressure of 2 millibars and a base temperature of up to 120° C. 64 g (25.6 weight %) distillate (29.3 weight % acetic acid, 70.3 weight % acetic anhydride and 0.4 weight % ethylidene diacetate) and 186 g distillation residue which contained 0.525 g rhodium and 161 g N,N-dimethylimidazolium iodide (=1.96 weight % Rh-carbonyl complex and 64.4 weight % DMII, based on 250 g catalyst solution) were obtained. The distillation residue was comminuted and introduced with agitation into 4500 ml water at 20° C. After 30 minutes, the suspension was heated to 60°–70° C. while agitation was continued. After altogether 1.5 hours, the remaining residue was filtered, after-washed with water and dried at 120° C. under 2 millibars, 25 g weighed material was obtained. Analysis indicated that it contained 0.525 g rhodium. This residue was placed in a Soxhlet-apparatus and freed from undistillable organic contaminants by extraction with 500 ml diethylether at the boiling point of the ether. After extraction over a period of 3 to 5 hours and drying, 6 g ether-insoluble residue was obtained. It contained 0.520 g rhodium, corresponding to a yield of 99%. The ether-insoluble residue contained practically all of the rhodium carbonyl complex used in the purification. It was recycled into the reaction.

The diethylether phase was evaporated and 19 g undistillable organic contaminants (=7.6 weight %, based on 250 g catalyst solution) were retained in the flask. Analysis indicated that the residue still contained 0.026 weight % rhodium. The ether phase distilled off was used again for extraction.

The water phase originating from the filtration was worked up under reduced pressure so as to recover the organic promoter. After evaporation of the water, 160.5 g N,N-dimethylimidazolium iodide, corresponding to a yield of 99.7%, was obtained, N/I-analysis with 12.5 weight % N and 56.7 weight % iodine and IR-analysis indicated that the organic promoter salt recovered was very pure. The organic promoter salt was recycled into the reaction and the water distilled off was used again for extraction.

EXAMPLE 4

250 g catalyst solution cycled for methyl acetate carbonylation was taken from the catalyst cycle consisting of palladium carbonyl complex, tri-n-butylmethylphosphonium iodide as organic promoter, undistillable organic contaminants, acetic acid, acetic anhydride and ethylidene diacetate, and freed from distillable matter at a base temperature of up to 120° C. and under a reduced pressure of 2 millibars. 80 g (32 weight %) distillate (51.9 weight % acetic acid, 10 weight % acetic anhydride and 38.1 weight % ethylidene diacetate) and 170 g distillation residue containing 0.85 g palladium and 152 g tri-n-butylmethylphosphonium iodide (=2 weight % Pd-carbonyl complex and 60.8 weight % TBMPI, based on 250 g catalyst solution) were obtained. The distillation residue was comminuted and introduced with agitation into 5000 ml water at 20° C. After 30 minutes, the suspension was heated to 65° C. while agitation was continued. After altogether 1.5 h, the residue was filtered, after-washed with water and dried at 120° C. under 2 millibars. 18 g weighed material which contained 0.846 g palladium was obtained. This water-insoluble residue was placed in a Soxhlet-apparatus and freed from undistillable organic contaminants by extraction with 500 ml diisopropylether at the boiling temperature of the ether. After extraction over 4 hours and drying, 7 g ether-insoluble residue was obtained. It contained 0.84 g palladium, corresponding to a yield of 98.8%. The ether-insoluble residue contained practically all of the palladium carbonyl complex used in the purification and was reused as such in the reaction.

The diisopropylether phase was evaporated and 11 g undistillable organic contaminants (=4.4 weight %, based on 250 g catalyst solution) which contained 0.03 weight % Pd were retained in the flask. The ether distilled off was used again for extraction.

The water phase originating from the filtration was worked up under reduced pressure to recover the organic promoter. After evaporation of the water, 151 g tri-n-butylmethylphosphonium iodide, corresponding to a yield of 99.3%, was obtained. The organic promoter salt was recycled to the carbonylation reaction and the water distilled off was used again for extraction.

We claim:

1. In a process for purifying and recovering constituents from a contaminated catalyst solution which is obtained as a result of the carbonylation of methyl acetate, dimethylether, or a mixture of methylacetate and dimethyl ether, the contaminated catalyst solution containing carbonyl compounds of noble metals of group VIII of the Periodic System of the elements, quaternary heterocyclic aromatic nitrogen compounds or quaternary organophosphorus compounds as organic promoters, undistillable organic contaminants, and volatile constituents, including acetic acid, acetic anhydride and ethylidene diacetate, the improvement which comprises: distillatively freeing the catalyst solution from the volatile constituents and water-treating the remaining solid distillation residue, the noble metal/carbonyl-compound being thereby precipitated together with the organic contaminants and the organic promoter becoming dissolved in the water; removing the precipitated and contaminated noble metal/carbonyl-compound by filtration and freeing it from the organic contaminants by extraction with aliphatic ethers; recovering the organic promoter from the water; and recycling the purified noble metal/carbonyl-compound and the recovered organic promoter into the carbonylation reaction.

2. A process as claimed in claim 1 wherein the organic promoter is recovered from the water by evaporating the water.

3. A process as claimed in claim 1 wherein the organic promoter is recovered by extracting it with halogenated hydrocarbons and evaporating said halogenated hydrocarbons.

4. A process as claimed in claim 1 wherein the distillation residue is water treated at 40° to 80° C.

5. A process as claimed in claim 1 wherein 10 to 100 parts by weight water are used per part by weight distillation residue.

6. A process as claimed in claim 1 wherein the noble metal/carbonyl-compound filtered off is extracted with diethyl- or diisopropylether.

7. A process as claimed in claim 1 wherein the catalyst solution additionally contains carbonyl-forming non-noble metals as inorganic promoters which, during said water-treatment of said solid distillation residue, are precipitated together with said organic contaminated noble metal/carbonyl-compound, filtered off, purified by extraction with an ether and recycled together with said noble metal/carbonyl-compound to the carbonylation reaction.

8. A process as claimed in claim 1 wherein the catalyst solution additionally contains carbonyl-forming non-noble metals as inorganic promoters which, during said water-treatment of said solid distillation residue, are dissolved together with said organic promoter, recovered by evaporation of the water and recycled together with said organic promoter to the carbonylation reaction.

9. A process as claimed in claim 8 wherein the organic promoter is also recovered from the water by evaporation of the water.

10. In a process for purifying and recovering constituents from a contaminated catalyst solution which is obtained as a result of the carbonylation of methyl acetate, dimethylether, or a mixture of methylacetate and dimethylether, the contaminated catalyst solution containing carbonyl compounds of noble metals of group VIII of the Periodic System of the elements, quaternary heterocyclic aromatic nitrogen compounds or quaternary organophosphorus compounds as organic promoters, undistillable organic contaminants, and volatile constituents including acetic acid, acetic anhydride and ethylidene diacetate, the improvement which comprises: distillatively freeing the catalyst solution from the volatile constituents and water-treating the remaining solid distillation residue, the noble metal/carbonyl-compound being thereby precipitated together with the organic contaminants and the organic promoter becoming dissolved in the water; removing the precipitated and contaminated noble metal/carbonyl-compound by filtration and freeing it from the organic contaminants by extraction with aliphatic ethers; removing the organic promoter by extracting it with halogenated hydrocarbons and evaporating said halogenated hydrocarbons; and recycling the purified noble metal/carbonyl-compound and the recovered organic promoter into the carbonylation reaction.

11. A process as claimed in claim 10 wherein the quaternary organophosphorus compounds are recovered from their aqueous solution by extraction with methylene chloride or chloroform.

12. A process as claimed in claim 10 wherein the catalyst solution additionally contains carbonyl-forming non-noble metals as inorganic promoters which, during said water-treatment of said solid distillation residue, are dissolved together with said organic promoter, recovered by extraction with halogenated hydrocarbons and evaporation of said halogenated hydrocarbons, and recycled together with said organic promoter to the carbonylation reaction.

13. A process as claimed in claim 10, wherein the distillation residue is water treated at 40° to 80° C.

14. A process as claimed in claim 10, wherein 10 to 100 parts by weight water are used per part by weight distillation residue.

* * * * *